United States Patent
Jana et al.

(10) Patent No.: US 9,439,739 B2
(45) Date of Patent: Sep. 13, 2016

(54) METHOD OF PRODUCING A DENTAL RESTORATION, DENTAL RESTORATION AND USE THEREOF

(75) Inventors: Carsten Jana, Jena (DE); Holger Hauptmann, Sindelsdorf (DE); Bernd K. Burger, Alling (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 1021 days.

(21) Appl. No.: 13/128,280

(22) PCT Filed: Oct. 21, 2009

(86) PCT No.: PCT/US2009/061502
§ 371 (c)(1),
(2), (4) Date: Aug. 1, 2011

(87) PCT Pub. No.: WO2010/053698
PCT Pub. Date: May 14, 2010

(65) Prior Publication Data
US 2011/0275031 A1    Nov. 10, 2011

(30) Foreign Application Priority Data
Nov. 10, 2008  (EP) .................................. 08168721

(51) Int. Cl.
*A61C 13/00*     (2006.01)
*A61C 13/083*    (2006.01)

(52) U.S. Cl.
CPC ....... *A61C 13/0006* (2013.01); *A61C 13/0022* (2013.01); *A61C 13/0835* (2013.01)

(58) Field of Classification Search
USPC ...................................................... 264/605
See application file for complete search history.

(56) References Cited

U.S. PATENT DOCUMENTS

| 4,176,706 A | 12/1979 | Been |
| 4,461,618 A * | 7/1984 | DeLuca et al. ............ 433/200.1 |

(Continued)

FOREIGN PATENT DOCUMENTS

| DE | 19944130 | 4/2001 |
| DE | 102005034803 | 3/2006 |

(Continued)

OTHER PUBLICATIONS

Partial European Search Report, EP 08168721, Dated May 12, 2009, 5 pages.

(Continued)

*Primary Examiner* — Angela Ortiz
*Assistant Examiner* — Russell Kemmerle, III (57) ABSTRACT

The invention relates to a method of producing a dental restoration (40), the method comprising the steps of providing a metallic frame (21) having an inner and an outer surface, applying one or more opaque layer(s) (23) or composition on the outer surface of the metallic frame, providing a facing precursor (31) having a volume A, mating the facing precursor on the outer surface of the metallic frame coated with the opaque layer using a mating composition to obtain a dental restoration intermediate, firing the dental restoration intermediate to a temperature where the facing precursor sinters to obtain a sintered facing having the volume B, and optionally applying a stain and/or glacing layer on the outer surface of the sintered facing. The invention also relates to a dental restoration obtainable by such a process.

8 Claims, 4 Drawing Sheets

(56) References Cited

U.S. PATENT DOCUMENTS

| | | | |
|---|---|---|---|
| 8,211,356 B1* | 7/2012 | Hartnett et al. | 264/663 |
| 8,409,491 B1* | 4/2013 | Stackpoole et al. | 264/624 |
| 8,568,649 B1* | 10/2013 | Balistreri et al. | 264/642 |
| 2006/0122719 A1* | 6/2006 | Kopelman et al. | 700/98 |
| 2006/0257824 A1* | 11/2006 | Pfeiffer et al. | 433/218 |
| 2009/0026643 A1* | 1/2009 | Wiest et al. | 264/16 |
| 2010/0015572 A1 | 1/2010 | Dierkes | |
| 2010/0248189 A1 | 9/2010 | Burger | |
| 2012/0015327 A1* | 1/2012 | Burger et al. | 433/202.1 |

FOREIGN PATENT DOCUMENTS

| | | |
|---|---|---|
| DE | 10 2006 033 794 | 3/2008 |
| EP | 1250895 | 10/2002 |
| WO | WO 94-27517 | 12/1994 |
| WO | WO 2008-009495 | 1/2008 |

OTHER PUBLICATIONS

Extended European Search Report, EP 08168721, Dated Jul. 29, 2009, 10 pages.
International Search Report for PCT/US2009/061502, Mailing Date Mar. 4, 2010, 5 pages.
English Language Abstract for DE 19944130 dated Apr. 12, 2001.
English Language Abstract for DE 102005034803 dated Mar. 16, 2006.
English Language Abstract for DE 10 2006 033 794 dated Mar. 6, 2008.
English Language Abstract for EP 1250895 dated Oct. 23, 2002.
English Language Abstract for WO 2008-009495 dated Jan. 24, 2008.

* cited by examiner

METHOD OF PRODUCING A DENTAL RESTORATION, DENTAL RESTORATION AND USE THEREOF

CROSS REFERENCE TO RELATED APPLICATIONS

This application is a national stage filing under 35 U.S.C. 371 of PCT/US2009/061502, filed Oct. 21, 2009, which claims priority to EP Application No. 08168721.2, filed Nov. 10, 2008, the disclosure of which is incorporated by reference in its/their entirety herein.

FIELD OF THE INVENTION

The invention generally relates to dental restorations comprising a metallic frame and a facing, including methods for making dental restorations, such as bridges, crowns, or abutments, e.g. from glass or glass ceramic materials.

BACKGROUND OF RELATED ART

In the field of dentistry, restoration of a patient's tooth or teeth that have, for example, been affected by caries generally includes the replacement of the natural tooth substance by an artificial substance. For larger restorations, pre-finished dental restorations or prostheses are commonly used to replace at least a part of the tooth or teeth.

Dental restorations or prostheses are often made as a two or more component configuration, with the individual components providing different characteristics for the restoration. For example, a frame may provide excellent structural support, and a facing may provide excellent aesthetics. The frame generally is a supporting structure for the dental restoration that provides mechanical stability and usually comprises an interface by which the restoration can be affixed to a prepared tooth of a patient. The facing provides for pleasing aesthetic characteristics that gives the restoration the shape and appearance of natural teeth. In addition, both the frame and the facing are shaped to fit well with the adjacent and opposed teeth in a patient's mouth.

In the recent years ceramic materials have been widely used for making high-quality dental restorations because of their good physical, aesthetic and biological properties. These restorations are often manufactured by an automated process, which typically includes:
- capturing data representing the shape of a patient's teeth, for example by scanning a plaster model of the patient's teeth or alternatively by scanning the actual teeth in the patient's mouth;
- designing the shape of a frame based on the captured data using software, such as computer-aided design (CAD) software; and
- manufacturing the frame to correspond to the designed shape, for example, by an automated Computer Numerical Controlled (CNC) machine.

There are approaches to integrating the steps of capturing, designing and manufacturing in a Computer Integrated Manufacturing (CIM) system. An exemplary CIM system for making frames for dental restorations is available from 3M ESPE AG (Seefeld, Germany) under the trade designation LAVA™.

Although such CIM systems would allow the manufacture of an integrated dental restoration (frame and facing together, in the example mentioned above), it is difficult to provide a single ceramic material that provides both the necessary structural durability and good aesthetics. Therefore the CIM system is normally used to manufacture the frame from a ceramic material that provides the required mechanical durability without regard to its aesthetic properties, after which a final layer or facing is applied to the frame to provide the necessary aesthetic properties. A facing of this type is very often manually prepared by skilled dental technicians, for example by manually applying several layers of a polymeric material or a glass-ceramic material, to provide the appropriate color, translucency, and other properties.

Another common method for manually preparing a facing is the "press over" technique. A frame is manufactured as described above, and manually covered with a wax layer or "wax-up" 300 with an outer surface that corresponds to the desired final shape of the tooth. That wax-up is used to form a pattern for a mold. The mold is then heated in a furnace so that the wax is burned off, and the frame remains as a core in the mold. The space between the core and the interior of the mold is then filled with a molten glass-ceramic material that is, for example, obtained from melting a ceramic pellet in channel or previously molten and poured into the channel, where it flows around the frame and fuses with the frame to form the facing. The restoration may then be removed from the mold, polished as necessary, and provided to the dentist for application to the patient's tooth.

Other methods of preparing dental restorations are described, for example, in DE 10 2005 034 803 A1, and DE 19 944 130 A1.

DE 10 2006 033 794 B3 describes a indirect route by milling a wax veneer and subsequently investing, burn-out the wax and pressing the veneer porcelain in the lost form.

WO 2008/009495 is directed to a set of elements for producing a dental prosthesis comprising a framework and one or more model parts for defining parts of the outer contour of a veneer for the framework. The model parts are typically made of wax and are burnt during the production of the dental prosthesis.

Although the current approaches for manufacturing of dental restorations may provide a variety of advantages, there is still a desire for a method of manufacturing an entire high-quality dental restoration in a cost efficient manner.

If possible, the dental restoration should be durable and have less defects or cracks.

SUMMARY OF THE INVENTION

In a first aspect the present invention provides a method of producing a dental restoration, the method comprising the steps of
- providing a metallic frame having an inner and an outer surface,
- applying one or more opaque layer(s) on the outer surface of the metallic frame,
- providing a facing precursor having a volume A, the facing precursor preferably being a machined article,
- mating the facing precursor on the outer surface of the metallic frame coated with the opaque layer using a mating composition to obtain a dental restoration intermediate,
- firing the dental restoration intermediate to a temperature where the facing precursor sinters to obtain a sintered facing having the volume B, and
- optionally applying a stain and/or glacing layer on the outer surface of the sintered facing, wherein volume A of the facing precursor is larger than volume B of the sintered facing.

A further aspect of the invention is directed to a dental restoration obtainable by the method described in the text of the invention.

The invention also features the use of a facing precursor as described in the text of the invention for producing a dental restoration comprising a metallic frame applied with an opaque layer.

Unless otherwise specified, within the context of the text of the invention, the following terms have the following meanings.

The term "dental restoration" means any restoration which can be used in the dental field. In this respect, the dental restoration shall have sufficient strength. Dental restorations are typically comprised of at least two parts: a dental framework (frame) and a dental veneer (facing). Examples include crowns, inlays, onlays, abutments and bridges (including 2, 3, 4, 5, 6, 7 or even 8 parts bridges).

The term "facing" within the meaning of this invention refers to the aesthetic part of a dental restoration, meaning the part comprising an outer surface of the finished restoration. The facing is further adapted to be applied to a frame which forms another part of the dental restoration, and the dental restoration is in turn applied to a tooth. The facing is preferably arranged at those parts of the frame that are likely to be visible in a patient's mouth, or that in particular functionally co-operate with the adjacent or opposed teeth of a patient, for example. A "facing precursor" refers to the facing in a pre-stage, that is, to a stage, where the facing is not finished yet. A facing precursor has a 3-dim. shape and is made of or comprises a certain material. The shape of the facing precursor corresponds essentially to the shape of the finished facing, however, is typically enlarged at least with respect to the outer, visible surface. Thus, the facing precursor has a solid consistency and is machinable. The facing precursor is neither a liquid, suspension nor a slurry.

A "machinable article" is an article having a 3-dimensional shape and having sufficient strength to be machined in a controlled and target-orientated way. That is, material parts of the machinable article can be removed in order to obtain another 3-dimensional shape, which remains dimensional stable for further machining, if desired. Machining comprises milling, grinding, cutting, carving, or shaping a material by a machine. A "machined article" is an article which has a 3-dimensional shape and which has been machined before further use.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

"Glass" means an inorganic non-metallic amorphous material which is thermodynamically an undercooled and frozen melt.

"Glass-ceramic" means an inorganic non-metallic material where one or more crystalline phases are surrounded by a glassy phase.

"Ceramic" means an inorganic non-metallic material that is produced by application of heat. Ceramics are usually hard and brittle and, in contrast to glasses or glass ceramics, display an essentially purely crystalline structure.

The term "proportionally enlarged" means that each of the three dimensions of an enlarged object is enlarged relative to the corresponding dimension of the original object by preferably substantially the same magnification factor. Further, "proportionally enlarged" may include tolerances of the magnification factor in each dimension so that each of the three dimensions of the enlarged object may be enlarged relative to the corresponding dimension of the original object by three individual magnification factors with at least two of the individual magnification factors being different from each other by about 1% to about 5%.

The term "proportionally reduced" means that each of the three dimensions of a shrunken object is reduced relative to the corresponding dimension of the original object by preferably substantially the same shrinkage factor. Further, "proportionally reduced" may include tolerances of the shrinkage factor in each dimension so that each of the three dimensions of the shrunken object may be reduced relative to the corresponding dimension of the original object by three individual shrinkage factors with at least two of the individual shrinkage factors being different from each other by about 1% to about 5%.

By "machining" is meant milling, grinding, cutting, carving, or shaping a material by a machine. Milling is usually faster and more cost effective than grinding.

A "powder" means a dry, bulk solid composed of a large number of very fine particles that may flow freely when shaken or tilted.

"Density" means the ratio of mass to volume of an object. The unit of density is typically g/cm$^3$. The density of an object can be calculated e.g. by determining its volume (e.g. by calculation or applying the Archimedes principle or method) and measuring its mass.

"Sintering" means making objects from a powder, by heating the material (typically below its melting point—solid state sintering) until its particles adhere to each other.

A "liquid" within the meaning of the invention is any solvent or liquid which is able to at least partially disperse or dissolve the inorganic binder at ambient conditions (e.g. 23° C.).

An article is classified as "opaque" within the meaning of the invention, if the article is essentially impenetrable to visible light. An opaque object is neither transparent (allowing all light to pass through) nor translucent (allowing some light to pass through). An opaque substance transmits very little light, and therefore reflects, scatters, or absorbs most of it.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. Ideally the composition or solution does not contain the said component at all. However, sometimes the presence of a small amount of the said component is not avoidable e.g. due to impurities contained in the raw materials used.

"Ambient conditions" invention mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

The facing provided by the invention is advantageous in comparison to conventionally prepared facings because it is more homogeneous and comprises less imperfections or defects. Defects may for example occur at the mating area of the facing and the frame. Without wishing to be bound to a certain theory, it is assumed that this is caused by the fact that the facing is typically manufactured under standardized manufacturing conditions and from a material having a substantially homogeneous structure, in contrast to having a dental technician manually layering a facing.

Furthermore, according to the invention, an existing milling system can be used not only to manufacture a ceramic frame but also the facing. This substantially reduces the time needed to prepare a dental restoration, and also provides a synergistic effect in that the data of the CAD/CAM system used for making the frame can also be used for designing and manufacturing of the facing.

It was also found that a facing precursor comprising an open-celled material may facilitate to reduce the milling time, because milling of a sintered glass ceramic tended to cause chippings at the facing precursor so that the milling speed preferably would be reduced to avoid such chippings.

Making a facing of an open-celled, for example pre-sintered, material also provides the advantage that the facing can be assembled with the frame essentially without trapping air between the parts because air can escape through the open-celled material.

Further, as a mating composition is used to assemble the facing precursor and the frame to form a dental restoration precursor, components of the mating composition may be enabled to escape through the open-celled material of the facing precursor. For example, because the mating composition typically comprises a liquid (for example for making the mating composition workable or applicable to a desired surface) the liquid may evaporate through the open-celled material of the facing precursor. Therefore, the time required to dry the mating composition in a dental restoration precursor prior to sintering may be reduced by the present invention.

Consequently, such a method has the advantage of providing a good bond between the facing and the frame because air and/or vapor (produced by the mating composition), that could keep the mating parts at least partially separate, is minimized.

Furthermore, because of the essential absence of air and/or vapor in the structure of the dental restoration, the strength and durability of the final dental restoration is high.

Thus, the present invention facilitates dental technicians to produce dental restorations with high quality in a time- and cost-saving manner.

Moreover, it was found that the invention is useful for all common dental alloys (precious as well as non-precious) having a coefficient of thermal expansion in the range of from about $9.6*10^{-6}K^{-1}$ to about $17.3·10^{-6}K^{-1}$.

Generally the use of a pre-sintered material for the facing precursor may facilitate machining, rather than grinding, because the pre-sintered material has a relatively low material strength. Further, an open-celled material may provide for applying a facing to a frame substantially without trapping air and therefore may provide for good durability of the dental restoration.

DETAILED DESCRIPTION OF THE INVENTION

In a first aspect the present invention provides a method for producing a dental restoration.

The method comprises the following step:

Providing a metallic frame having an inner and an outer surface.

In the context of the invention, a metallic frame functions as support structure for the facing. Metallic frame and facing are two major components of the final restoration. The metallic frame is typically manufactured by the "lost wax" method, known to the person skilled in the art.

Thus, the metallic frame may be casted from metal or a metal alloy, or may be machined therefrom. The material the frame is made of typically provides relatively good mechanical stability.

The metallic frame can be characterized by at least one of the following features:

The coefficient of thermal expansion of the metal the metallic frame is made of typically ranges from about $9.6*10^{-6}K^{-1}$ to about $17.3*10^{-6}K^{-1}$. Other suitable ranges include from about $9.6*10^{-6}K^{-1}$ to about $15.2*10^{-6}K^{-1}$ and $13.8*10^{-6}K^{-3}$ to about $15.2*10^{-6}K^{-1}$ and $16*10^{-6}K^{-1}$ to about $17.3*10^{-6}K^{-1}$.

The metallic frame comprises metals selected from the group consisting of Ti, Au, Pt, Pd, Ag, Zn, Co, Cr, Mo, W, Ni and combinations and alloys thereof.

The metallic frame is typically comprised of or consists of metal only or of a metal alloy. Commercially available metal alloys which were found to be useful for the present invention include e.g. those described in Table 1 below.

TABLE 1

| Supplier | Alloys with high fraction of noble metals | Alloys with reduced fraction of noble metals | Titanium | Palladium based alloys | Non-precious alloys |
|---|---|---|---|---|---|
| Argen | Argedent 90 | Argedent Euro | | Argelite 61 | Argeloy N.P. Special |
| Wieland | Porta ™ PK | Porta ™ SMK | | Simidur ™ S2 | |
| Bego | PontoStar H | BegoCer G | | BegoPal | Wirobond ™ 280 |
| Dentaurum | Triloy | | rematitan ® M | | Remanium ® CS |
| DeguDent ™ | Degudent ™ G | Degudor ™ | | | |

The method of producing a dental restoration further comprises the following step:

Applying an opaque layer on the outer surface of the metallic frame.

The opaque layer can be applied once, twice or even more times on the outer surface of the metallic frame, typically with a firing step between.

An opaque layer is not applied for esthetic reasons only, that is, to give the metallic frame a more pleasant appearance. A further aspect can be seen in the fact that the opaque layer functions as thermal isolator, at least to some extent, during the final sintering step. The opaque layer may facilitate a smooth heat transfer between the different materials used for preparing the dental restoration, i.e. the metallic frame, the mating composition and the facing precursor, which usually comprises a glass ceramic material.

A further aspect of the opaque layer can be seen in bridging the coefficients of thermal expansion of the metal frame and the mating material.

The composition used for applying the at least one opaque layer typically comprises a glass or glass-ceramic material, an opaquer agent and optionally a liquid (e.g. water, ethanol).

A typical composition of the glass or glass-ceramic used can comprise about 40 wt.-% to about 60 wt.-% of silica, about 8 wt.-% to about 18 wt.-% of alumina, about 5 wt.-% to about 15 wt.-% of potassium-oxide, about 2 wt.-% to about 10 wt.-% of sodium-oxide, about 0 wt.-% to about 5 wt.-% of lithium-oxide, about 0 wt.-% to about 5 wt.-% of calcia, about 0 wt.-% to about 5 wt.-% of barium-oxide about oxide about 0 wt.-% to about 2 wt.-% cerium-oxide or cerium-fluoride and 0.2 wt.-% to about 25 wt.-% of pigments.

A useful opaquer agent may typically include metal oxides like zirconia, tin oxide, titanium oxide, mixtures and combinations thereof.

The value of the coefficient of thermal expansion of the opaque layer is typically greater than the value of the thermal expansion coefficient of the facing (e.g. about $0.5*10^{-6}K^{-1}$ above).

The opaque layer is typically applied on the surface of the metallic frame by using a brush or by spraying. The composition to be applied can be provided as a powder/liquid combination to be mixed before application or as a paste in a ready to use form.

Usually, after the application of the at least one opaque layer, the coated metallic frame is fired in an oven (e.g. "Dekema Austromat 3001" from Dekema Dental Keramikofen GmbH, Freilassing, Germany) at a temperature above about 900° C. or above about 950° C. A useful firing process includes the steps: preheat temperature: about 400° C.; closing time: about 6 min; heating rate: about 80 K/min; firing: 950° C. for 1 min. The process is preferably carried out under vacuum conditions between 450° C. and 949° C. One, two or more opaque layers can be applied and the firing step repeated, if desired.

The method of producing a dental restoration further comprises the following step:

Providing a facing precursor having a volume A,

The facing precursor typically comprises an open-celled and pre-sintered material. The facing precursor may also consist essentially of, or consist of, an open-celled pre-sintered material.

The facing and the facing precursor as referred to in this specification preferably comprise a glass or glass ceramic material or may consist essentially of, or consist only of, a glass or glass ceramic material.

The glass or glass ceramic material is preferably selected to be compatible for use in human bodies. Furthermore, the glass ceramic material is preferably selected to provide good aesthetic appearance for the dental restoration, in particular when combined with a frame. An exemplary formulation for a glass or glass ceramic as it may be used with the present invention comprises about 60 wt.-% to about 70 wt.-% of silica, about 9 wt.-% to about 15 wt.-% of alumina, about 5 wt.-% to about 10 wt.-% of potassium-oxide, about 9 wt.-% to about 15 wt.-% of sodium-oxide, about 0 wt.-% to about 1 wt.-% of lithium-oxide, about 2 wt.-% to about 5 wt.-% of calcia, about 1 wt.-% to about 2 wt.-% of barium-oxide, about 0 wt.-% to about 1 wt.-% of zirconium oxide and about 0 wt.-% to about 1 wt.-% cerium-oxide or cerium-fluoride.

Glass or glass ceramic materials which may, for example, be used for manufacturing a blank and/or a facing precursor are generally available under the designations:

"VMK 95" and "Omega 900" from Vita Zahnfabrik, Bad Säckingen, Germany;

"IPS Classic" and "IPS d.Sign" from Ivoclar Vivadent, Principality of Liechtenstein;

"Vintage" from Shofu, Japan; and

"REFLEX" from Wieland GmbH & Co.KG, Pforzheim, Germany.

Preferably the facing precursor has a shape that corresponds to a proportional enlargement of the facing with a magnification factor of preferably between about 1.05 and about 2.2, in more particular between about 1.05 and about 1.8, more preferably between about 1.12 and about 1.5.

The facing precursor typically comprises an inner surface corresponding to a proportionally dimensioned counter-surface of an outer surface of a frame. The inner surface of the facing precursor may be scaled so that it matches the outer surface of the frame when the facing precursor has been sintered.

During sintering, the material of the facing precursor typically shrinks toward the inner surface of the facing precursor with the inner surface generally maintaining its shape.

The facing precursor is typically produced by machining a blank comprising a glass or glass ceramic containing material.

Machining the facing precursor for making a facing, typically comprises the step of controlling a CNC machine based on data related to the shape of the facing precursor which are obtained from a CAD system, wherein the facing precursor is proportionally enlarged with respect to the facing.

Typically a blank of an open-celled and pre-sintered material is provided by the steps of:
 pressing an amount of particles together to form a material body, and
 pre-sintering the material body at a temperature of between about 500° C. and about 750° C. to form the blank.

A blank may have a size of between about 20 mm and about 30 mm in two dimensions, for example may have a diameter in that range, and may be of a certain length in a third dimension. A blank for making single crowns may have a length of between about 15 mm and about 30 mm, and a blank for making bridges may have a length of between about 40 mm and about 80 mm. A typical size of a blank as it can be used for making single crowns has a diameter of about 24 mm and a length of about 19 mm. Further, a typical size of a blank as it can be used for making bridges has a diameter of about 24 mm and a length of about 58 mm.

As mentioned above, providing the facing precursor typically includes removing material from a blank to form a facing precursor. Material may be removed from the blank by machining, for example, by grinding, milling, or a combination of both. Preferably the removal of material is performed by milling the shape of the facing precursor from the blank. The removal of material from a pre-sintered material takes relatively little effort relative to material removal from the same material after it has been sintered, because the pre-sintered material has a relatively low strength compared to sintered material. As a result, milling (rather than grinding) can be used to remove material from a blank, which is usually faster and more cost effective.

In a further embodiment of the invention, the pre-sintered material of the facing precursor may be wax impregnated, meaning that wax at least partially fills the cells of the pre-sintered material. A wax impregnation improves stability of the material blank in order to prevent breakage of the blank during milling. In more detail, the wax impregnation may dampen vibrations of the blank during milling or reduce dust. During the sintering process of the facing, the impregnated wax can be burned off or melted.

The average size of the particles forming the pre-sintered material of the facing precursor as referred to in this specification is typically in a range of about 10 µm to about 60 µm, and preferably about 30 µm. The distribution of the particle size may be for example:
 10% of the particles smaller than about 3 µm;
 50% of the particles smaller than about 26 µm; and
 90% of the particles smaller than about 71 µm.

In more particular the average particle size which the pre-sintered material referred to in this specification is comprised of may be about 20 µm, for example according to a particle size distribution in which:
 10% of the particles are smaller than about 1.2 µm;
 50% of the particles are smaller than about 10 µm; and
 90% of the particles are smaller than about 45 µm.

The volume of the cells in the pre-sintered material relative to the total volume of the pre-sintered material as referred to in this specification is typically in a range of about 20% to about 40%, and more preferably in a range of about 30% to about 38%.

To obtain samples having different porosities the samples can be pre-sintered to different degrees as described in the following.

The samples can be uniaxially pressed from a powder of a glass or glass ceramic material. The pressed samples typically have a pressed density which is in the range of about 1.3 g/cm$^3$ to about 1.6 g/cm$^3$ in the range of about 1.4 g/cm$^3$ to about 1.6 g/cm$^3$ or in the range of about 1.34 g/cm$^3$ to about 1.42 g/cm$^3$. Each pressed sample can be pre-sintered at ambient pressure of about 101.3 kPa in a process that comprises the steps of:
(1) heat the sample from room temperature (e.g. about 23° C.) to about 620° C. at a heating rate of about 3 K/min and
(2) exposing the sample at the temperature of about 620° C. for a dwell time period of about 30 min;

According to a particular embodiment, a glass ceramic material found to be useful includes powder of a commercially available glass ceramic material that comprised 55 wt.-% to 75 wt.-% of silicon oxide, 8 wt.-% to 22 wt.-% of aluminum oxide, 0 wt.-% to 8 wt.-% of boron oxide, 2 wt.-% to 12 wt.-% of potassium oxide, 4 wt.-% to 12 wt.-% of sodium oxide, 0.01 wt.-% to 5 wt.-% of strontium oxide, 0.1 wt.-% to 2 wt.-% of cerium oxide, 0.01 wt.-% to 2 wt.-% of tin oxide, 0 wt.-% to 3 wt.-% of zinc oxide, 0 wt.-% to 4 wt.-% of phosphor oxide, 0 wt.-% to 3 wt.-% of calcium oxide, 0 wt.-% to 3 wt.-% of lithium oxide, and 0 wt.-% to 1 wt.-% of fluoride.

According to a preferred embodiment, the glass ceramic material used for producing the facing can be characterized by at least one of the following features:
 Density: about 2.1 to about 2.8 g/cm$^3$ or about 2.2 to about 2.6 g/cm$^3$ and/or
 Glass transition temperature: about 500 to about 600° C. or about 520 to about 580° C., preferably about 550° C.

The facing as it is referred to in this specification may be substantially free of cells, however may comprise up to about 16 cells per mm$^2$. Preferably, the facing may comprise about 4 to about 8 cells per mm$^2$. The cells preferably have a diameter of less than about 150 µm, and more preferably a diameter of less than about 100 µm and most preferably a diameter of less than about 40 µm. In a particular embodiment the facing has less than about 16 cells per mm$^2$ with a diameter of less than about 150 µm, wherein not more than about 6 cells have a diameter of between about 40 and about 150 µm. The unit "cells per mm$^2$" is related to the number of cells present on a cross section according to the test method as defined in DIN 13925.

The facing precursor preferably comprises an open-celled material. The term "open-celled" within this context typically relates to an "open porosity" according to the mercury porosimetry as defined in DIN 66133 of between about 6% and about 35%, in particular of between about 15% and about 35%, and in more particular of between about 30% and about 35%.

The volume of the facing precursor can be determined by different means. One possibility is to calculate the volume based on the weight of the facing taking the density of the material, the facing is made of, into account. The density of the material, the facing is made of, on the other hand can be determined by providing a regular shaped sample (e.g. a cube or a cuboid) and determining the weight of this sample.

Another possibility is to determine the volume of the open cells of the facing precursor e.g. by mercury porosimetry as specified in DIN 66133 (thereby obtaining volume 1) and further to determine the volume of remaining parts of the facing precursor containing closed cells and the solid material. This can be done e.g. by the Archimedes method (thereby obtaining volume 2). The total volume of the sample results from the summation of the values of volume 1 and volume 2.

The volume of the facing can be calculated as follows: [Volume of fired dental restoration (metallic frame+facing)]−[Volume of metallic frame]. This can be done e.g. by using the Archimedes method, as the fired dental restoration does not contain open cells anymore.

The raw breaking resistance of the pre-sintered material or the facing precursor as referred to in this specification is preferably in a range of about 3 to about 15 MPa, more preferably in a range of about 4 to about 12 MPa, and preferably about 5 MPa to about 9 MPa according to the "punch on three ball test" as specified in ISO 6872.

The bending strength of the sintered material or the facing as referred to in this specification is preferably in a range of about 50 to about 400 MPa, in more particular in a range of about 50 to about 120 MPa according to the "punch on three ball test" as specified in ISO 6872.

The material the facing is made of may be selected to provide a certain translucency. Typically the translucency is specified by the opacity of a material relative to daylight. Typical ranges of the opacity of the sintered material or the facing are 50% to 60% (typically corresponding to natural dental enamel), 60% to 80% (typically corresponding to natural dentine) and 80% to 90% (typically corresponding to natural opaque dentine).

The method further comprises the following step:
Matting the facing precursor on the outer surface of the metallic frame coated with the opaque layer using a mating composition to obtain a dental restoration intermediate.

The facing precursor is placed with its inner surface on an outer surface of the frame, typically coated with an opaque layer. The inner surface of the facing precursor may be a proportionally or similarly dimensioned counterpart to the outer surface of the frame, and more specifically the inner surface of the facing precursor may be a proportionally enlarged counterpart of the outer surface of the frame, to permit the former to fit over the latter with any appropriate clearance.

The facing precursor and the frame are fitted with a mating composition arranged between mated surfaces of the frame and the facing precursor.

Such a mating composition typically comprises a powdery glass or glass ceramic material, for example of the type used for the facing, which is mixed with liquid (e.g. water). The mating composition may fill a gap between mated surfaces of the facing precursor and the frame.

The mating composition may further provide for compensating tolerances within such gap. In case a dental restoration precursor formed by use of a mating composition is sintered, the mating composition typically dries during sintering and the remaining particles fuse and form an intermediate layer between the facing and the frame.

The mating composition may further comprise an organic or a polymeric binder to provide a good adhesion of the intermediate layer with adjoining surfaces, and may provide a certain elasticity of the intermediate layer. Such elasticity may, for example, help to make a dental restoration more durable, in particular to help prevent a facing from loosening from the frame.

Glasses or glass ceramics which can be used can be characterized by at least one of the following features:
Composition: 55 wt.-% to 75 wt.-% of silicon oxide, 8 wt.-% to 22 wt.-% of aluminum oxide, 0 wt.-% to 8 wt.-% of boron oxide, 3 wt.-% to 12 wt.-% of potassium oxide, 4 wt.-% to 12 wt.-% of sodium oxide, 0.01 wt.-% to 5 wt.-% of strontium oxide, 0.1 wt.-% to 2 wt.-% of cerium oxide, 0.01 wt.-% to 2 wt.-% of tin oxide, 0 wt.-% to 3 wt.-% of zinc oxide, 0 wt.-% to 4 wt.-% of phosphor oxide, 0 wt.-% to 3 wt.-% of calcium oxide, 0 wt.-% to 3 wt.-% of lithium oxide, and 0 wt.-% to 1 wt.-% of fluoride.
Coefficient of thermal expansion: about $8*10^{-6}K^{-1}$ to about $15.8*10^{-6}K^{-1}$ or $8*10^{-6}K^{-1}$ to about $9*10^{-6}K^{-1}$ (especially for metallic frames containing Ti and/or having a coefficient of thermal expansion in the range from about $9.6*10^{-6}K^{-1}$ to about $10*10^{-6}K^{-1}$) or about $12*10^{-6}K^{-1}$ to about $13.6*10^{-6}K^{-1}$ (especially for metallic frames having a coefficient of thermal expansion in the range from about $13.8*10^{-6}K^{-1}$ to about $15.2*10^{-6}K^{-1}$) or from about $15*10^{-6}K^{-1}$ to $15.8*10^{-6}K^{-1}$ (especially for metallic frames having a coefficient of thermal expansion in the range from about $16*10^{-6}K^{-1}$ to about $17.3*10^{-6}K^{-1}$).

It can be beneficial, if the value of the coefficient of thermal expansion of the facing or the material the facing is made of is smaller than the thermal expansion of the metallic frame or the material the metallic frame is made of. This may help to increase the compressive strength of the facing and might facilitate the provision of a durable dental restoration.

A typical mating composition can be the same glass or glass ceramic powder which is used for producing the facing precursor, mixed with a liquid comprising about 0.99 wt.-% polyglycol 4000 P (available from Clariant, under the Prod. code 109467), about 49.50 wt.-% 1,2 propandiol (available from Eissler Scientific) and de-ionized water ad to 100 wt.-%. The powder to liquid ratio is typically about 2:1 by weight. This mating composition can be applied to both parts to be mated with a slight surplus eventually needed for filling a gap between the facing precursor and the frame. Alternatively, the mating composition can only be applied to one of the two parts to be mated, preferably on the inner surface of the facing precursor.

The method of producing a dental restoration further comprises the following step:
Firing the dental restoration intermediate to a temperature where the facing precursor sinters to obtain a sintered facing having the volume B.

Sintering usually transforms the open-celled material of the facing precursor into a sintered material that forms the facing.

As the facing precursor has a volume A, which is larger than volume B of the sintered facing, the density of the facing precursor is typically smaller than the density of the sintered facing.

Thus, the facing precursor has a first material density and the facing has a second material density. In particular, the first and second densities may correspond to the densities of the materials the facing precursor and the facing, respectively, are comprised of. Preferably the second material density is higher than the first material density.

The sintered material referred to in this specification preferably has a material density in a range of about 2 g/cm³ to about 2.7 g/cm$^3$, and the pre-sintered material preferably has a material density in a range of about 30% to about 92% of the material density of the sintered material. Preferably the material density of the pre-sintered material is in a range of about 40% to about 60% of the material density of the sintered material, and more preferably in a range of about 45% to about 55%.

For example, the material density of the facing precursor (or of the pre-sintered material) may be in a range of about 0.6 g/cm$^3$ to about 1.8 g/cm$^3$ and the facing (or the sintered material) obtained from it may have a material density of about 2 g/cm$^3$. In another example the material density of the facing precursor (or of the pre-sintered material) may be in a range of about 0.8 g/cm$^3$ to about 2.5 g/cm$^3$ and the facing (or the sintered material) obtained from it may have a material density of about 2.7 g/cm$^3$. The facing precursor (or the pre-sintered material) may generally have a material density in a range of about 0.6 g/cm$^3$ to about 2.5 g/cm$^3$.

Typically the difference between the density of the facing precursor and the density of the facing (or of the pre-sintered material and the sintered material, respectively) is a result of the presence of a higher amount of cells within the facing precursor (or the pre-sintered material) than in the facing (the sintered material).

In a preferred embodiment of the invention, sintering the facing precursor comprises, consists essentially of, or consists of heating the facing precursor. Sintering may, for example, comprise heating the material to a temperature of between about 700° C. to about 1100° C. for a time of between about 1 to about 3 h. The facing precursor may further be sintered at an atmospheric pressure of between about 25 and about 50 mbar.

Sintering typically includes the densification of a porous material to a less porous material (or a material having less cells) having a higher density, in some cases sintering may also include changes of the material phase composition may occur (for example, a partial conversion of an amorphous phase toward a crystalline phase).

In an embodiment of the invention the facing precursor is dimensionally proportional to and larger than the facing, where the facing precursor is proportionally enlarged relative to the facing by a magnification factor of between about 1.05 and about 2.2 or between about 1.05 and about 1.6, or between about 1.12 and about 1.5.

Typically sintering results in the facing precursor shrinking proportionally. The shrinkage factor typically corresponds to the absolute value of the magnification factor. The facing therefore preferably has proportionally reduced dimensions relative to the facing precursor and the ratio of corresponding dimensions of the facing precursor and the facing is preferably between about 1.05:1 and about 2.2:1 or between about 1.05:1 and about 1.6:1 or between about 1.12:1 and about 1.5:1.

In a preferred embodiment the facing has a color within the range of colors of human teeth. The facing may be shaded in a manner so as to make the dental restoration resemble natural teeth, or it may be shaded so that the dental restoration when placed in a patient's mouth optically matches the natural tooth or teeth adjoining the dental restoration. Further, the facing preferably has a translucency similar of human teeth. The facing may comprise materials having different colors and a certain degree or certain degrees of translucency, for example, to provide an optical appearance resembling that of natural teeth.

According to a further embodiment the facing precursor can be provided by a method comprising the steps of:

forming an outer surface of the facing precursor based on a virtual model of an outer surface of the dental restoration; and forming an inner surface of the facing precursor based on a virtual model of an outer surface of a frame.

A virtual model is typically a dataset adequate to define a three-dimensional surface, for example a dataset usable with CAD software. The outer surface of the dental restoration may be designed with CAD software. Designing the outer surface of the dental restoration may include the use of standard surfaces obtained from a database, for example loaded from the database into the CAD software. Accordingly, the method of the invention may comprise the step of modeling the outer surface of the dental restoration on a CAD system, and modeling may include the use of data from a database that includes standard surfaces.

In an embodiment of the invention forming the outer surface of the facing precursor includes at least one procedure selected from scanning a patient's tooth, scanning a temporary restoration, and scanning a model of a patient's tooth. For example, the shape of a plaster model of a patient's teeth obtained from a dental impression may be captured by a scanner for scanning three-dimensional objects, for example one available from 3M ESPE AG, Seefeld, Germany under the designation LAVA™ Scan ST.

The shape of the plaster model thus may be transformed into a scan model of the patient's teeth, including the tooth to be restored. To the extent the tooth or teeth to be restored are preserved and therefore available at the plaster model the shape of those tooth or teeth maybe used to determine a part of the shape of the exterior surface of the dental restoration. Therefore an appropriate part of the scan model may be used as a partial virtual model of the exterior surface of the dental restoration. The other part of the virtual model which is not obtainable from scanning the plaster model may be added by design, for example by use of CAD software as described.

The outer surface of the dental restoration may also be largely or entirely designed, for example, in case large parts of the tooth or teeth are not available at the plaster model because tooth substance has been removed to prepare the tooth surface for receiving the restoration. To insure that the restoration that is applied to the patient's tooth or teeth fits and works well, the design of the outer surface of the dental restoration is preferably performed in view of the size, shape, and location of teeth that adjoin, cooperate with, or oppose the dental restoration. For example, the occlusal surfaces of an opposed tooth should readily mate with the occlusal surfaces of the restored tooth, which can be arranged by the appropriate design of the dental restoration in view of the opposed tooth or teeth.

In an alternative, a restoration model representing the final shape of the dental restoration may be applied on the plaster model. As a result, the desired outer surface of the dental restoration may be determined directly from the restoration model, and therefore can be directly obtained from scanning the plaster model including the restoration model. The restoration model may for example be a wax model which is manually shaped while on the plaster model of the remainder of the patient's teeth.

The outer surface of the frame may be obtained by scanning a pre-finished frame, or by retrieving data from a CAD software or system with which the frame has been designed.

The method of producing a dental restoration may further comprise the following step (optional):

Applying a stain or glacing composition on the outer surface of the sintered facing, A suitable glazing composition can be characterized by at least one of the following features:

Composition: 55 wt.-% to 75 wt.-% of silicon oxide, 8 wt.-% to 22 wt.-% of aluminum oxide, 0 wt.-% to 8 wt.-% of boron oxide, 3 wt.-% to 12 wt.-% of potassium oxide, 4 wt.-% to 12 wt.-% of sodium oxide, 0.01 wt.-% to 5 wt.-% of strontium oxide, 0.1 wt.-% to 2 wt.-% of cerium oxide, 0.01 wt.-% to 2 wt.-% of tin oxide, 0 wt.-% to 3 wt.-% of zinc oxide, 0 wt.-% to 4 wt.-% of phosphor oxide, 0 wt.-% to 3 wt.-% of calcium oxide, 0 wt.-% to 3 wt.-% of lithium oxide, and 0 wt.-% to 1 wt.-% of fluoride.

Coefficient of thermal expansion: smaller than the coefficient of thermal expansion of the facing (e.g. below about $0.5 \times 10^{-6} K^{-1}$ to about $1 \times 10^{-6} K^{-1}$).

Glazing the facing may be advantageous to achieve a good optical appearance of the dental restoration and/or to render the dental restoration more durable.

A further aspect of the invention is directed to a dental restoration obtainable by the method described in the text of the invention.

The dental restoration typically has the shape of a dental crown, dental bridge, abutments, inlay or onlay or parts and combinations thereof.

It has been found that if the various coefficients for thermal expansion of the various materials are within certain ranges or following a certain sequence or relation, then a reliable and durable dental restoration can be provided. A sequence or relation, which was found to be useful, is the following:

The coefficient of thermal expansion of the metallic frame is typically greater than the coefficient of thermal expansion of the opaque layer. The coefficient of thermal expansion of the opaque layer is typically greater than the coefficient of thermal expansion of the mating composition. The coefficient of thermal expansion of the matting composition is preferable equal to the coefficient of thermal expansion of the facing. The coefficient of thermal expansion of the facing is typically greater than the coefficient of thermal expansion of an optional glazing layer.

If these relations are followed, the compressive strength of the facing is usually increased, whereas the tensile stress is reduced or even eliminated. This facilitates the provision of a durable dental restoration showing less defects (e.g. like fractures).

Thus, if a small fracture occurs in the facing, the risk that the fracture moves forward and expands is reduced (e.g. due to the absence of tensile stress).

The invention also features the use of a facing precursor as described in the text of the invention for producing a dental restoration comprising a metallic frame, typically coated with an opaque layer.

With respect to the figures, preferred embodiments are described in further detail herein below.

Figure 1:
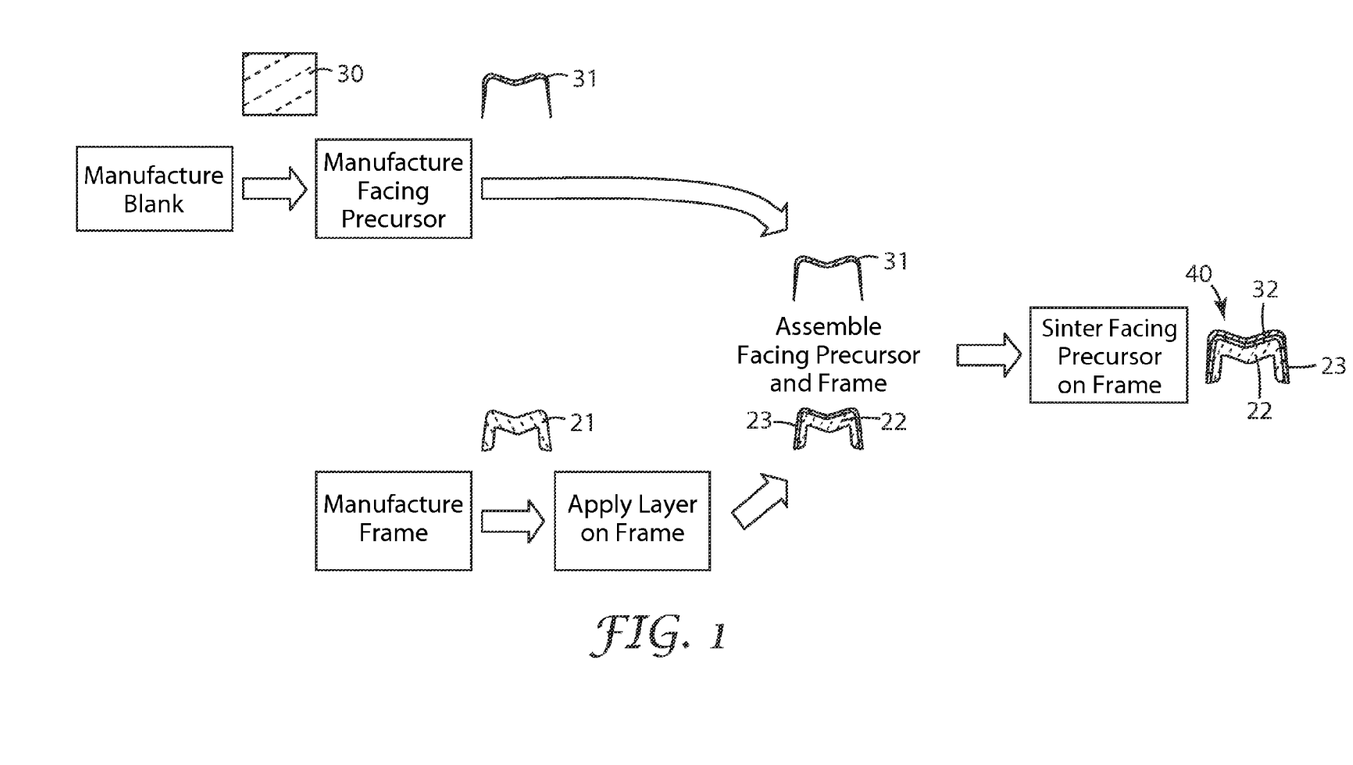
FIG. 1 is a flow diagram outlining an exemplary process for preparing a dental restoration according to an embodiment of the invention.

FIG. 1 gives an overview of an exemplary process to prepare a dental restoration according to an embodiment of the invention. Typically, the process starts with the preparation of the metallic frame 21 e.g. by the conventional "lost wax" technique.

The shape of the frame 21 may be designed with CAD software by an operator. The operator typically designs the frame 21 based on scan data obtained from capturing of a patient's teeth, for example by scanning a plaster model of the patient's teeth. It is also possible to make a model of the dental restoration and use the captured shape of the model for the design. Such model may, for example, be a wax model which is manually shaped by a dental technician. Alternatively, intra-oral scanning may be used, in which an image is captured directly from the patient's teeth, rather than from a model. These techniques are familiar to persons of skill in the field. On the outer surface of the frame 21 an opaque layer is applied and sintered to obtain frame 22 with the opaque layer fixed on top.

The preparation of the facing 32 will now be described. A blank 30 is provided made from an open-celled pre-sintered material from which a facing precursor 31 is formed. The facing precursor 31 is for example formed by milling it from the blank 30 with a CNC milling machine.

The shape of the facing precursor 31 may also be designed with CAD software. For example, the interior shape of the facing precursor may be designed based on the exterior shape of the frame 22, and the exterior shape of the facing precursor may be designed based on the exterior shape of the dental restoration 40. The shape of the frame 22 may be captured by scanning an available frame, or it may be available in the form of CAD data if the frame was designed with CAD software, for example. Further the shape of the frame 22 may be obtained partially or entirely from a database that includes standard frame shapes. The final shape of the dental restoration 40 may be designed based on a captured image or data set representing the shape of the patient's teeth, or based on a captured image or data set representing the shape of a model of the dental restoration, or based on shapes obtained from a library of images or data sets representing the shapes of various teeth.

On the basis of the shape of the frame and the shape of the final restoration the shape of the facing may be generated by the CAD system, so that the facing with its outer shape fits adjoining and cooperating teeth in the patient's mouth. Further, the shape of the facing is generated so that an inner surface of the facing fits with the outer shape of the frame.

The milled facing precursor 31 is then combined with the frame 22, and the facing-frame assembly is subsequently finally sintered to obtain the dental restoration 40. The sintering of the facing precursor 31 which is placed on the frame 22 is preferably performed at a temperature lower than the melting temperature of the frame 22, so that the frame 22 substantially maintains its shape and mechanically supports the facing precursor 31 that is softened during sintering. The mating composition is not shown.

Because the facing precursor typically shrinks during sintering the shape of the facing precursor usually is proportionally enlarged relative to the shape of the final facing. Alternatively, the facing 32 is sintered before it is combined with a sintered frame (diagram of the alternative not shown). In this case the facing precursor is milled to substantially its final shape.

The dental restoration 40 may be finally shaped, could be sandblasted and/or the surface may be at least partially finished with glaze.

Figure 2A:
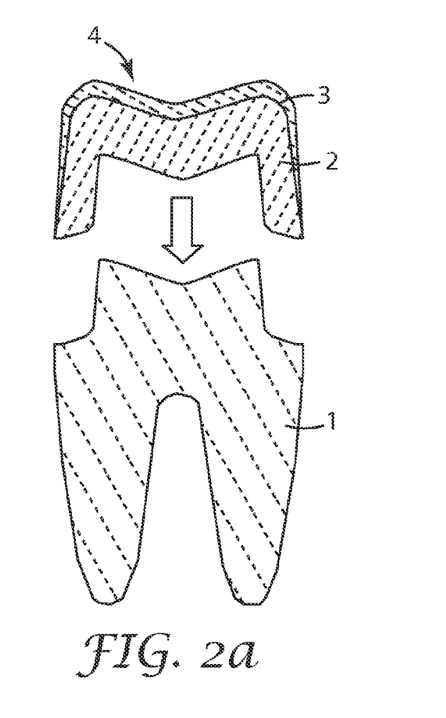
FIG. 2a, 2b are schematic cross-sectional views of an exemplary representation of a dental restoration according to an embodiment of the invention.
Figure 2B:
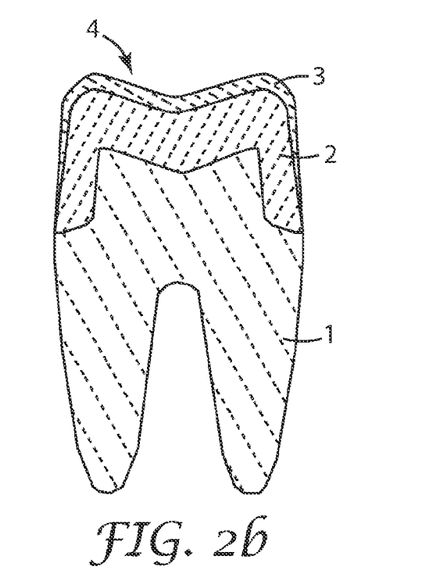

FIG. 2a and FIG. 2b are schematic cross-sectional views showing an exemplary representation of a dental restoration that includes a crown 4 made from a frame 2 and a facing 3. FIG. 2a illustrates the assembly of the crown 4 onto to a prepared natural tooth 1. The natural tooth 1 is prepared so that it consists essentially of healthy tooth substance and provides a solid support for receiving the crown 4. This preparation is typically done by removing any caries-infected tooth substance, and shaping the tooth by grinding to create a structure allowing for the support of and bonding to a dental restoration. The crown 4 is then assembled on the prepared tooth by mating opposed surfaces of the crown 4 with the surfaces of the prepared tooth 1. FIG. 2b shows the restored tooth. The crown 4 is affixed to the natural tooth 1, for example, with adhesive cement of the type available from 3M ESPE Dental of Seefeld, Germany, under the designation Ketac™ Cem Plus or RelyX™ Unicem.

Figure 3A:
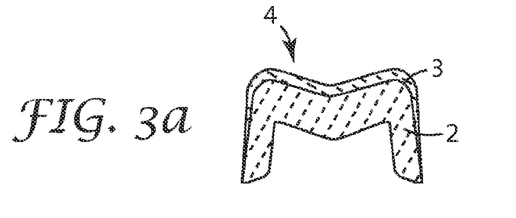
FIGS. 3a-3e are diagrams showing various representations of a dental restoration to which the invention is applicable according to an embodiment of the invention.
Figure 3B:
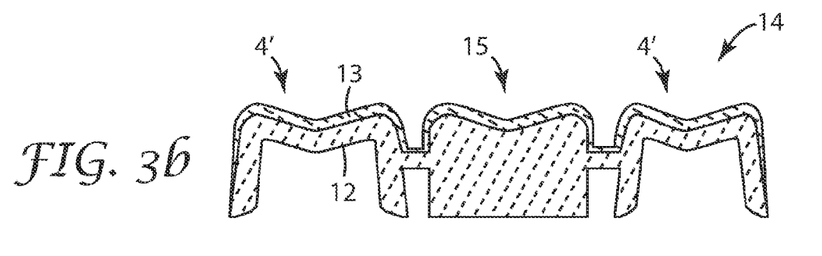

As shown in FIGS. 3a-3e, the dental restoration may be used to replace natural tooth substance to different extents, up to replacing an entire tooth or several teeth. FIG. 3a again shows crown 4 of FIG. 2 with the frame 2 and the facing 3. FIG. 3b shows a bridge 14 that basically consists of two crowns 4' connected with a pontic 15 that is designed to replace an entire absent tooth. The bridge has a frame 12 and attached to it a facing 13 prepared and applied in accordance with the invention. Therefore the bridge 14 spans an area where a natural tooth is missing. Typically a bridge extends from a prepared natural tooth, to a pontic, and then to another prepared natural tooth. A bridge can also be designed to replace two or more missing teeth, for example by including two or more pontics connected to each other in the same manner as the single pontic described above. A bridge may also have only one crown attached to only one natural tooth, for example in case a second natural tooth is not available or not suitable for attachment.

Figure 3C:
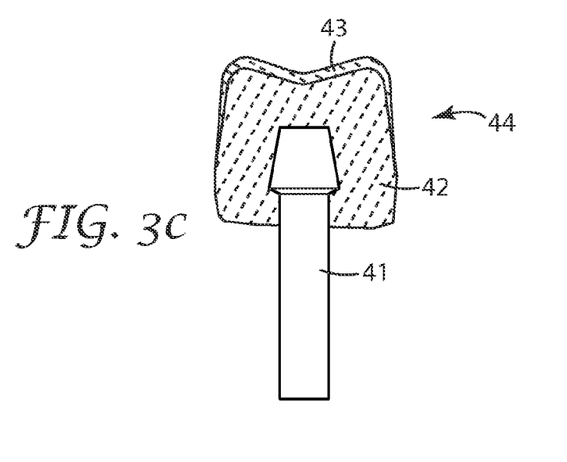

FIG. 3c shows as a further example of a dental restoration an abutment 44 having a facing 43 and a frame 42 prepared and applied in accordance with the invention. The abutment 44 is attached on a dental implant 41 that, for example, may be implanted in a patient's jaw. An abutment typically replaces an entire natural tooth and may be an alternative to a bridge. As an advantage relative to a bridge the abutment does not require the preparation of adjoining natural teeth and therefore helps to maintain the patient's natural teeth. An abutment may also replace two or more natural teeth and may be attached to two or more dental implants 41, however preferably two implants may provide sufficient fixation of an abutment replacing more than two teeth. The abutment may be connected with a pontic or may be part of a bridge, for example a bridge that extends from a dental implant, includes a pontic, and is connected to a crown that is bonded to a prepared tooth. Such a bridge may also have more than one pontic.

Figure 3D:
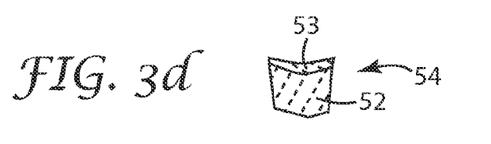
Figure 3E:
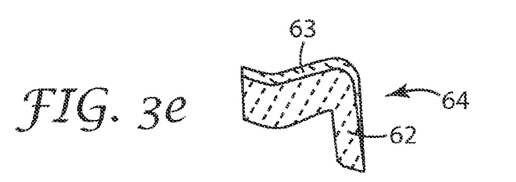

Finally, FIG. 3d shows an inlay 54 with a facing 53 attached to a frame 52, and FIG. 3e shows an onlay 64 with facing 63 attached to a frame 62 as further examples. The facings 53, 63 are prepared and applied in accordance with the invention. Inlays and onlays are typically used as smaller dental restorations. Typically an inlay replaces a part of an occlusal surface of a tooth and an onlay in addition replaces at least one side surface of a tooth. Inlays and onlays are typically alternatives to dental fillings, and are made for example of hardenable filling materials. They usually provide better aesthetic characteristics and better durability than normal filling materials.

Figure 4:
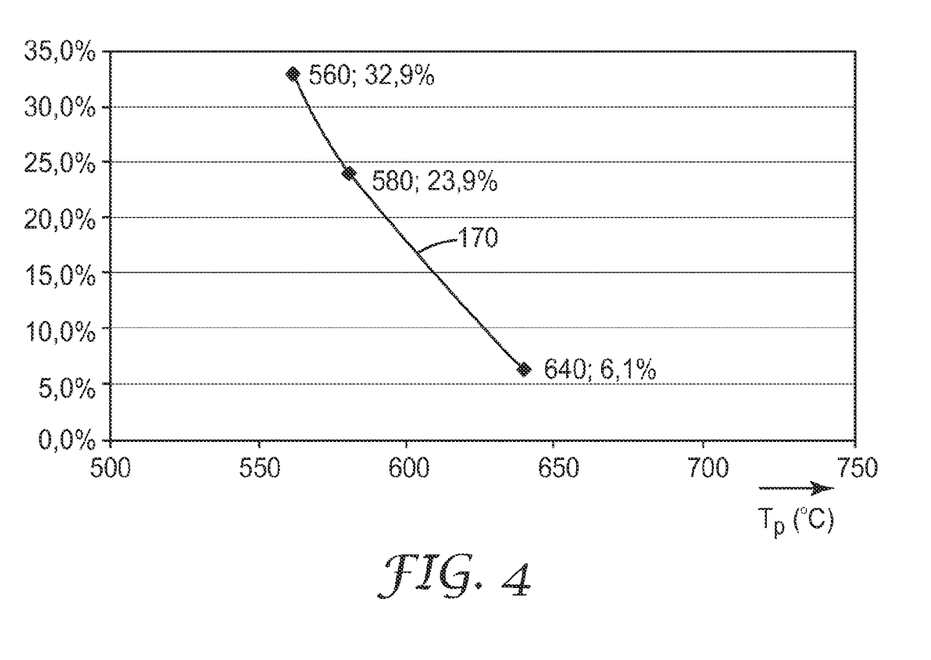
FIG. 4 is a diagram representing data measured at a reference glass ceramic material by use of the mercury porosimetry according to DIN 66133.

FIG. 4 is a diagram representing along the vertical axis the porosity or open porosity according to the mercury porosimetry as specified in DIN 66133. Along the horizontal axis a maximum pre-sintering temperature $T_p$ is represented. The diagram further shows a curve 170 that is based on measurements of the porosity or open porosity depending on the pre-sintering temperature $T_p$. The pre-sintering temperature referred to in the diagram is the maximum temperature at which samples used for the measurements were pre-sintered. The samples used were uniaxially pressed from a powder of the reference glass ceramic material as specified herein. The pressed samples had a pressed density which was in the range of about 1.34 g/cm³ and about 1.42 g/cm³. Each pressed sample was pre-sintered at ambient pressure of about 101.3 kPa in a process that comprised the steps of:

(1) heat the sample from room temperature of about 23° C. to about 620° C. at a heating rate of about 3 K/min;
(2) exposing the sample at the temperature of about 620° C. for a dwell time period of about 30 min;

The dental restoration of the present invention does typically not contain components or additives which jeopardize the intended purpose to be achieved with the present invention, i.e. providing an aesthetic and durable dental restoration. Thus, components or additives added in an amount which finally results in a non-tooth-coloured article are usually not contained in the final dental restoration. Typically, an article is characterized as tooth coloured if it can be allocated a colour from the Vita™ colour code system, known to the person skilled in the art.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

Although specific embodiments of the present invention have been described above in detail, it will be understood that this description is merely for purposes of illustration. Various modifications of and equivalents corresponding to the disclosed aspects of the preferred embodiments described above may be made by those skilled in the art without departing from the spirit of the present invention, which is defined by the following claims.

EXAMPLES

Firing was conducted in a commercially available sintering furnace ("Dekema Austromat 3001" from Dekema Dental Keramikofen GmbH, Freilassing, Germany).

1. Preparation of Frame

After modelling a frame in wax, the wax part was embedded in Stellavest (Company: GC) and burnt out. Following the "lost-wax" technique, Wirobond™ (Cobalt-Chrome-alloy, BEGO, Germany) was casted into the form in order to prepare the metal support structure. Then the metal support structure was sand-blasted ($Al_2O_3$, 110 µm, 3 bar).

2. Applying of Opaque Layer

An opaquer was prepared by mixing a powder with an opaquer liquid (2:1); Vita Omega 900 (VITA Zahnfabrik; Germany). The opaquer was applied with a brush on the top of the metal support structure and fired in a furnace. A second layer of opaquer was applied on the outer surface of the support structure and fired again.

3. Preparation of the Blank for Producing the Facing Precursor 100 g of Omega 900 EN3 (incisel mass) powder was mixed with 15 g de-ionised water and sieved using a sieve mesh 1000 µm. The obtained granulate was pressed to blocks (5 bar, 10 s holding time), dried and sintered at 640° C. for 30 min in an oven.

Then the block was glued into a LAVA™ frame (3M ESPE; Germany).

4. Construction of Facing Precursor

On top of the opaque layer, a removable waxup was modelled. Using LAVA™ Design software (3M ESPE;

Germany), the frame with the opaque layer was scanned as well as the final contour of the tooth (using the waxup scan function). These scans delivered the milling parameter for the veneer. Milling was carried out on a LAVA™ milling machine (3M ESPE; Germany) using the standard program for zirconia veneers.

5. Mating

A mixture was prepared using Vita Omega 900 DA3 powder (VITA Zahnfabrik; Germany) and a liquid comprising about 0.99 wt.-% polyglycol 4000 P (Clariant), about 49.50 wt.-% 1,2 propanediol (Eissler Scientific) and deionized water ad to 100 wt.-%. The powder to liquid ratio was 2:1 by weight. Then the facing precursor was filled to ⅔ with the mating composition and put on top of the metallic frame coated with the opaque layer. The dental restoration intermediate was laid on a water absorbing paper. After 2-3 min drying time, an excess of mating composition was removed and missing mating composition was added. After drying, the dental restoration intermediate was fired in an oven.

After cooling, the dental restoration was grinded with common diamond tools and veneer porcelain was added. Then a second firing step was performed.

6. Final Glaze

| Preheat temp. | Drying time | Closing time | Heating rate | Firing temp. | Soaking time | Vacuum at firing temp. |
|---|---|---|---|---|---|---|
| 600° C. | — | 4 min | 75 K/min | 890° C. | 1 min | Yes |

The invention claimed is:

1. A method of producing a dental restoration, the method comprising the steps of
    providing a metallic frame having an inner and an outer surface,
    applying one or more opaque layer(s) on the outer surface of the metallic frame,
    providing a facing precursor having a volume A, the facing precursor having a 3-dimensional shape, an inner and an outer surface, the inner surface corresponding to a proportionally dimensioned countersurface of the outer surface of the metallic frame,
    mating the facing precursor on the outer surface of the metallic frame applied with the opaque layer using a mating composition to obtain a dental restoration intermediate, the mating composition comprising a glass or glass ceramic material and a liquid,
    firing the dental restoration intermediate to a temperature where the facing precursor sinters to obtain a sintered facing having a volume B, and
    wherein volume A of the facing precursor is larger than volume B of the sintered facing.

2. The method of claim 1, wherein the metallic frame is characterized by at least one of the following features:
    coefficient of thermal expansion of the material the metallic frame is made of: from about $9.6*10^{-6} K^{-1}$ to about $17.3 \cdot 10^{-6} K^{-1}$ and
    comprising metals selected from the group consisting of Ti, Au, Pt, Pd, Ag, Zn, Co, Cr, Mo, W, Ni, alloys and combinations thereof.

3. The method according to claim 1, wherein the opaque layer is characterized by at least one of the following features:
    comprising a glass or glass-ceramic material, an opaquer agent and optionally a liquid and
    coefficient of thermal expansion of the opaque layer is greater than the value of the thermal expansion coefficient of the sintered facing.

4. The method according to claim 1, wherein the mating composition is characterized by at least one of the following features:
    comprising a glass or glass ceramic powder, a liquid and a binder and
    coefficient of thermal expansion of the sintered mating composition is essentially equal to the coefficient of thermal expansion of the sintered facing.

5. The method according to claim 1, wherein the facing precursor is characterized by at least one of the following features:
    the facing precursor comprising an open-celled material,
    the facing precursor comprising a glass or glass ceramic material,
    the facing precursor having a first material density and the sintered facing having a second material density, wherein the second material density is higher than the first material density and
    the facing precursor being proportionally enlarged relative to the sintered facing by a magnification factor of between 1.12 to 1.5.

6. The method of claim 1, wherein the facing precursor is obtainable by a method comprising the steps of
    forming an exterior surface of the facing precursor based on a virtual model of an exterior surface of the dental restoration and
    forming an interior surface of the facing precursor based on a virtual model of an exterior surface of a frame.

7. The method of claim 6, wherein forming of the exterior surface of the facing precursor includes at least one procedure selected from scanning a patient's tooth, scanning a temporary restoration, and scanning a model of a patient's tooth.

8. The method according to claim 1, wherein the facing precursor is obtainable by a process comprising the step of:
    controlling a CNC machine based on data related to the shape of the facing precursor which are obtained from a CAD system, wherein the facing precursor is enlarged with respect to the facing.

* * * * *